United States Patent [19]

Renzel et al.

[11] 4,432,235

[45] Feb. 21, 1984

[54] ULTRASONIC INSTRUMENT WITH TIME AND AMPLITUDE GATE BAR DISPLAY

[75] Inventors: Peter Renzel, Düren; Hanno Jacobs, Langenfeld, both of Fed. Rep. of Germany

[73] Assignee: Krautkramer-Branson, Inc., Lewistown, Pa.

[21] Appl. No.: 402,152

[22] Filed: Jul. 26, 1982

[30] Foreign Application Priority Data

Oct. 5, 1981 [DE] Fed. Rep. of Germany ....... 3139570

[51] Int. Cl.³ ............................................ G01N 29/04
[52] U.S. Cl. ........................................ 73/611; 73/606;
 73/610; 73/614; 340/715; 340/722; 328/115
[58] Field of Search ................. 73/620, 610, 611, 614;
 328/115, 150; 340/721, 722, 715

[56] References Cited

U.S. PATENT DOCUMENTS 3,474,438 10/1969 Lauher .............................. 340/722
3,924,078 12/1975 Bussey ............................... 340/700
4,373,394 2/1983 Renzel et al. ....................... 73/611

Primary Examiner—Howard A. Birmiel
Attorney, Agent, or Firm—Ervin B. Steinberg; Philip J. Feig

[57] ABSTRACT

An ultrasonic test instrument includes a pulse generator, a receiver, a cathode ray tube screen display and a time gate means providing a gated time interval for viewing only echo signals which arise from a predetermined workpiece region under test. The time gated interval is shown as a horizontal gate bar display on the screen and the length of the bar being indicative of the gated time interval. Circuitry provided generates a reference signal to cause the gate bar to appear at a height commensurate with the echo signal received in the gated intervals having the highest peak amplitude. Unless reset, the amplitude of the gate bar remains at this peak value although subsequent echo signals may have a lower amplitude.

9 Claims, 13 Drawing Figures

ULTRASONIC INSTRUMENT WITH TIME AND AMPLITUDE GATE BAR DISPLAY

BRIEF SUMMARY OF THE INVENTION

This invention relates to an ultrasonic instrument for nondestructive testing of workpieces, comprising a screen for displaying ultrasonic signals reflected by defects in a workpiece and a time gate for evaluating the defect responsive ultrasonic echo signals wherein the time gate is shown on the screen in the form of a bar (gate bar) of variable position and variable length, the length of the gate bar corresponding to the duration of the time gate and the height of the bar corresponding to a reference voltage representing maximum echo pulse amplitude.

In the nondestructive testing of workpieces by ultrasonic pulses, it is conventional to use electronic time gates for selecting transit time ranges corresponding to specific depth ranges in the workpiece under test. The echo pulses can then be evaluated separately for each transit time range. For example, one gate can be used for a defect responsive echo signal arising within a certain depth range and another gate for the rear wall echo. During the test, the test probe is usually moved over the surface of the workpiece. Ultrasonic pulses are transmitted and received at intervals of a few hundredths to a few thousandths of a second. The only perceptible result on the screen of the ultrasonic device is a fluctuation of the pulse display caused by the motion of the test probe. The probe position at which the maximum pulse amplitude occurs within a predetermined depth range is particularly important. During manual testing, therefore, the test probe is moved backwards and forwards over the workpiece and, if required, rotated around its longitudinal axis until the maximum pulse amplitude has been determined. This process of determining the maximum echo pulse amplitude is essential in evaluating defects in the workpiece and requires relatively high operator attention while viewing the screen. The fluctuations in pulse amplitude are very fast and the maximum value can easily pass unnoticed. During the motion of the test probe, the peak value of the pulse amplitude is very frequently exceeded and has to be produced anew. There is no direct comparison between the assumed maximum values occurring at different times. A frequent remedy is to mark temporarily the perceived maximum value with a grease pencil on the screen of the display tube until a still higher value, if any, is discerned. This method of testing is complicated and time consuming. In order not to be distracted by spurious ultrasonic pulse displays, threshold values are set for the depth range under investigation and only pulse amplitudes which exceed the set threshold value are displayed, see "Ultrasonic Testing of Materials" (book) by J. & H. Krautkramer, 2nd ed. Springer-Verlag, Berlin, Heidelberg, New York (1977), page 247. U.S. patent application Ser. No. 199,244 of P. Renzel et al, filed Oct. 21, 1980 entitled "Display of Ultrasound Test Data", now U.S. Pat. No. 4,333,345 dated June 8, 1982 also describes a method and circuit by means of which the height of the threshold value and the depth range of interest can be adjusted and can be displayed as a bar on the screen with the adjusted co-ordinate values. However it is not possible with these known methods to automatically determine and indicate the peak amplitude of a number of ultrasonic signals received successively.

Another known circuit designed to determine and display the peak value of a number of successively received ultrasonic pulses is shown in Japanese patent application No. 53-125285. To this end, the entire transit time range to be tested is divided into a number of partial ranges and in each range an amplitude counter counts the amplitudes and stores both the time and the amplitude information, the amplitude counter being constructed so that it counts only upwards (forwards). A manual switch is used to recall the stored information and display it on the screen of an ultrasonic instrument. A disadvantage of the last mentioned arrangement is that a switch has to be actuated before the amplitude of the hitherto maximum ultrasonic pulse is displayed on the screen. In addition, only a maximum echo which has once occured is reproduced and displayed on the screen. It is impossible to follow the increase in echo amplitude or the change therein. The known devices are also disadvantageous in that relatively complex switching circuitry is required.

An object of the present invention is the provision of a switching means which is simpler than that in known instruments and which simplifies the process of reading the peak amplitudes of a number of successively received ultrasonic echo signals.

A particular advantage of the invention is that the peak value of the various echo amplitudes resulting from the back and forth motion of the test probe over the workpiece surface is not only determined but is also continuously displayed.

Other details and advantages of the invention will be readily apparent from the embodiments which are explained with reference to the drawings.

DETAILED DESCRIPTION OF THE INVENTION

Figure 1A:
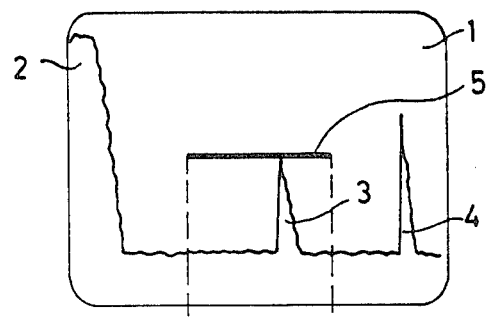
FIGS. 1a to 1d show the use of the gate bar of an ultrasonic instrument for indicating the peak amplitudes of ultrasonic signals.

FIG. 1 depicts a display screen 1 of an ultrasonic instrument, showing an ultrasonic pulse display of the kind normally visible on the screen during testing of workpieces. The drawing shows a transmitter pulse 2 appearing on screen 1, a reflector echo (or defect echo) 3 resulting from a flaw, and an echo 4 resulting from the rear wall of the workpiece. A gate bar 5 variable in height, lateral position and length is also visible on screen 1. The length of bar 5 corresponds to the time gate (defect expectation range) t2–t1. The height of bar 5 according to the invention is equal to the height of the peak value of all defect echo amplitudes 3 received in the predetermined measuring range as determined by the setting of a time gate.

Figure 1B:
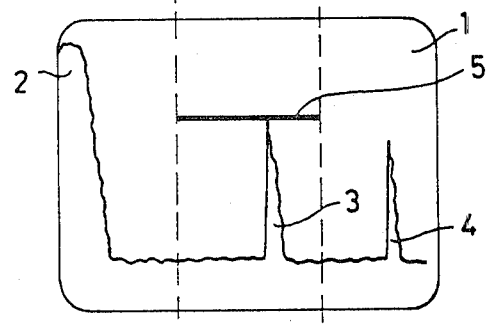
Figure 1C:
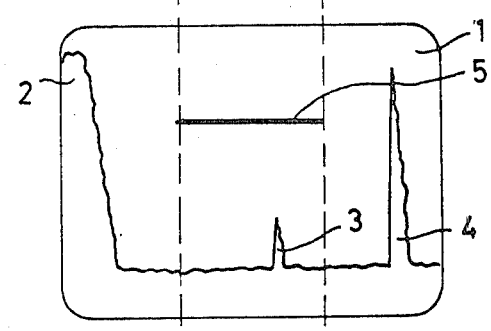
Figure 1D:
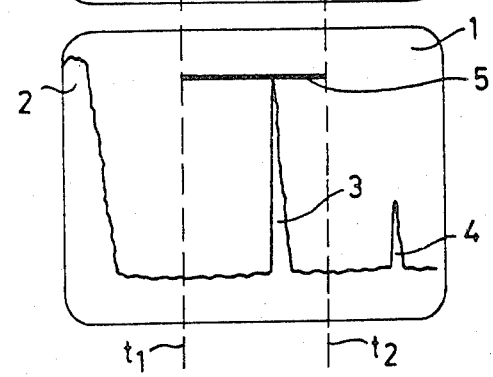

If, therefore, during a test, the test probe is moved over the surface of the workpiece relative to a defect, an echo from the defect is received at the corresponding time in the form of a pulse display 3. If the pulse display occurs in the preselected time gate t2–t1, a bar display according to the invention appears at the peak of the pulse display. The length of the bar corresponds to the duration of time gate t2–t1. If the displayed pulse has a higher amplitude during subsequent motion of the probe, the bar rises to the peak of the pulse (FIG. 1b). If, on the other hand, the pulse amplitude becomes lower during subsequent motion of the test probe (FIG. 1c) the bar remains at its previous amplitude as long as the peak of the pulse remains below the bar during motion of the test probe. If a still higher pulse is displayed during subsequent motion of the test probe (FIG. 1d), the bar, according to the invention, moves to the peak of the higher pulse. During a test, therefore, the bar will always indicate the maximum echo pulse amplitude reached heretofore.

Figure 2:
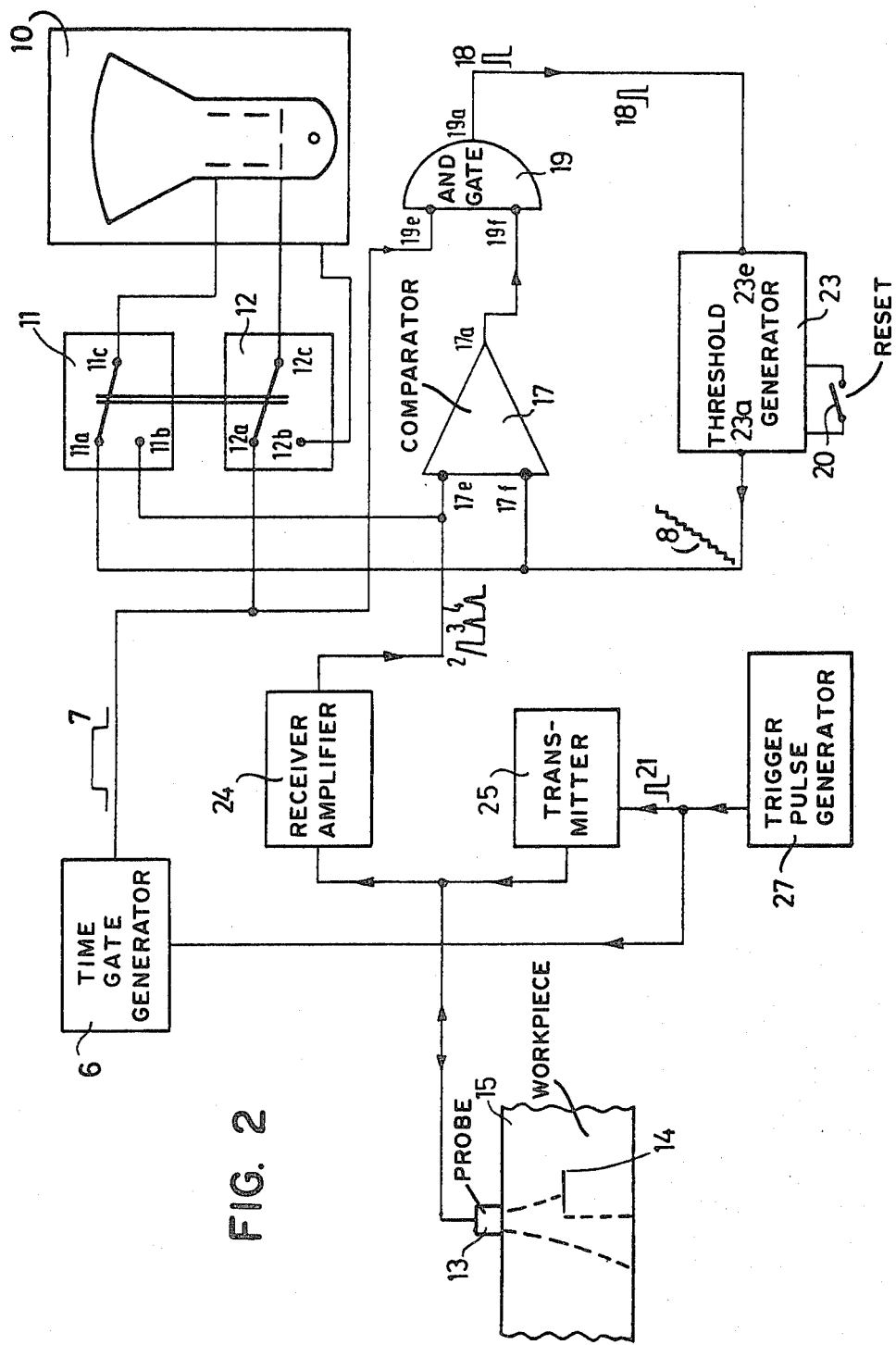
FIG. 2 is a block circuit diagram of an embodiment of the present invention.

FIG. 2 shows a preferred embodiment of the circuit for varying the height of the gate bar in dependence on the received echo amplitude. The figure shows a trigger pulse generator 27 (clock), an ultrasonic pulse transmitter 25 and a receiver amplifier 24. The transmitter output and the receiver input are connected to a test probe 13 coupled to workpiece 15. The circuit also comprises a time gate generating unit 6, a comparator 17, a threshold voltage generator 23, an AND gate 19, switches 11 and 12, and a display means 10 which includes a cathode ray tube.

Trigger pulse generator 27 provides periodic pulses 21 for triggering the ultrasonic pulse transmitter 25, thus energizing the probe 13 so that it transmits ultrasonic search pulses. The echo pulse produced by a reflector 14 in workpiece 15 and the echo signal from the rear wall of the workpiece are, in the present example, received by the same probe 13 after the passage of the respective transit times of the pulses, and are converted into electric pulses and amplified in the receiver amplifier 24. With regard to the present invention it does not matter whether the echo pulses are received by the same probe 13 or by other probes. Trigger pulse 21 also actuates the time gate unit 6 which generates the time gate pulse 7. The length and the start of the gate pulse 7 are advantageously selectable and, as shown in FIG. 1, are represented by time points t1 and t2.

If, for example, a defect responsive pulse 3 occurs for the first time during the time in which pulse 7 is present (open gate condition) set pulses 18 are produced as will be described hereinafter. The set pulses are supplied to input 23e of the threshold generator 23. A reference or comparison voltage 8 appears at the output 23a of the threshold generator 23 and such voltage 8 increases by one digital step with each set pulse 18. The reference voltage 8 is supplied to one input 17f of comparator 17 whereas the other input 17e of the comparator 17 is supplied with echo responsive pulses 2, 3, 4 amplified by amplifier 24. Consequently, the pulses are available at the comparator output 17a when the pulses 2, 3, 4 at the comparator input 17e have peak values which are higher than the value of the reference voltage 8 at the input 17f. The pulses delivered by the comparator 17 are supplied to one input 19f of the AND gate 19 whereas its other input 19e is supplied with the time gate pulse 7 from the time gate generator 6. Consequently, the AND gate transmits from among the pulses at input 19f of the gate 19 only that pulse which is present during the time gate pulse 7, i.e. pulse 3 in the present example. Pulse 3 is supplied as the set pulse 18 to the threshold generator input 23e.

If, as a result of a corresponding number of set pulses 18, the reference voltage 8 is one digital step higher than one of the peak values of pulses 2, 3, or 4, the comparator 17 will block the pulse and not produce a pulse at its output during such time. If this is the case for pulse 3, no pulse will be transmitted by the AND gate during the time t1 to t2 determined by gate pulse 7. The other pulses do not need to be considered here, since they likewise cannot pass through the AND gate. If however no further set pulse 18 is generated, the threshold generator 23 cannot increase the reference voltage 8 at its output. When, and only when, a pulse 3 occuring during the interval of gate signal 7 has a higher peak value than the corresponding reference voltage 8, will a set pulse 18 again be generated and the reference voltage 8 be increased until it is again one digital step higher than the peak value of the pulse. By means of a suitable electronic first switch 11, the signal amplifier of the cathode ray tube display stage 10, i.e. preferably the Y-amplifier, is connected cyclically and alternately to (a) the output of the receiver amplifier 24 for providing the pulse displays 2, 3, 4 and (b) to the reference voltage 8 for indicating the highest peak which has heretofore occurred within the time gate signal 7. As a result, screen 1 of the cathode ray tube display stage 10 shows a horizontal bar at the height equal to the highest peak pulse amplitude displayed heretofore. In order to display the pulse on the screen when the first switch 11 is in the corresponding position, a second switch 12 is used to intensify the screen display during the entire line sweep of stage 10, whereas when switch 11 is in the other position, the screen display is intensified only during the gate interval, preferably by pulse 7. As a result the bar appears on the screen only during gate signal 7, i.e. during the time gate interval t1 to t2.

A switch 20 can be used to reset the threshold generator for starting a new measuring process with the reference voltage 8 starting at a minimum value.

Figure 3:
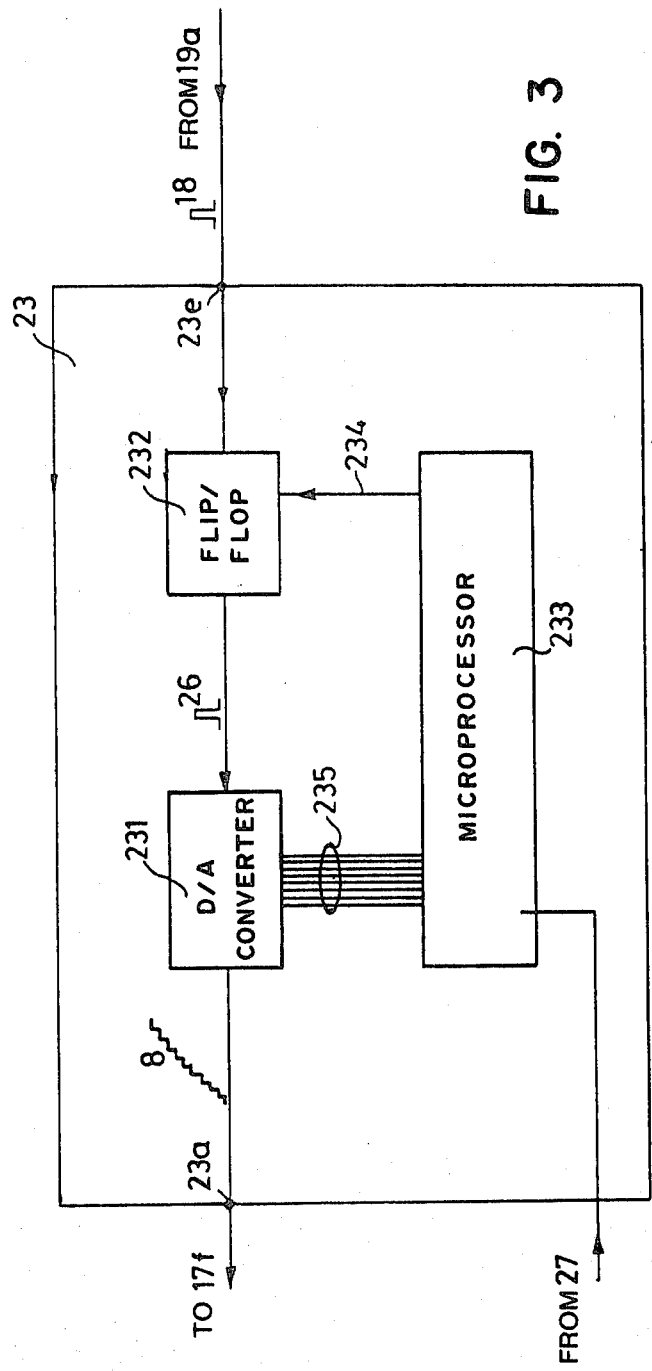
FIG. 3 is a block circuit diagram of the threshold generator used in FIG. 2.

In an embodiment of the invention according to FIG. 3 the threshold generator 23 comprises a D/A converter 231, a flip-flop 232 and a microprocessor 233. Preferably, the set pulses 18 generated by the AND gate 19 are first supplied to the flip-flop 232. The flip-flop is reset by the microprocessor via conductor 234 responsive to the occurrence of each trigger from the trigger generator 27. Flip-flop 232 generates a pulse 26 which is supplied as a set pulse to the D/A converter, thus increasing the reference voltage 8 by a digital step. If voltage 8 is a digital step higher than the amplitude of the ultrasound pulse 3, comparator 17 becomes blocked. As previously described, no new set pulse 18 is generated and the flip-flop 232 is not set and accordingly does not deliver a set pulse to the D/A converter 231.

When, and only when, a pulse 3 having a higher peak value than the corresponding reference voltage 8 occurs during the time of gate pulse 7, is the flip-flop 232 set again and the reference voltage 8 increased until it is again one digital step higher than the peak value of pulse 3.

FIG. 4 shows another embodiment of the invention for the rapid adjustment of the reference voltage 8 to the peak value of a pulse. As shown, voltage 8 is already set at half the maximum possible pulse height, FIG. 4a.

Figure 4A:
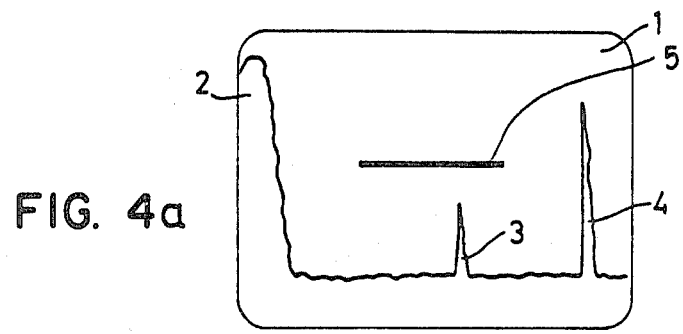
FIGS. 4a to 4d illustrate the preadjustment of the gate bar by successive approximation.
Figure 4B:
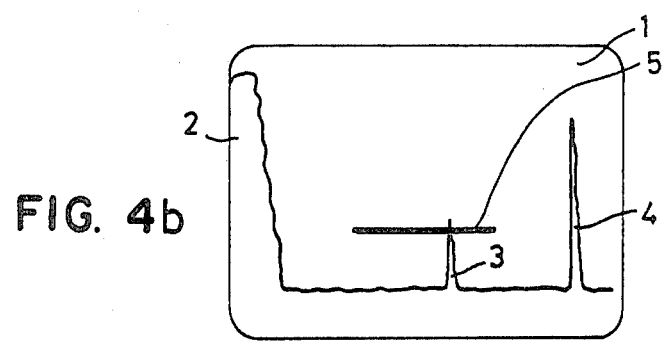
Figure 4C:
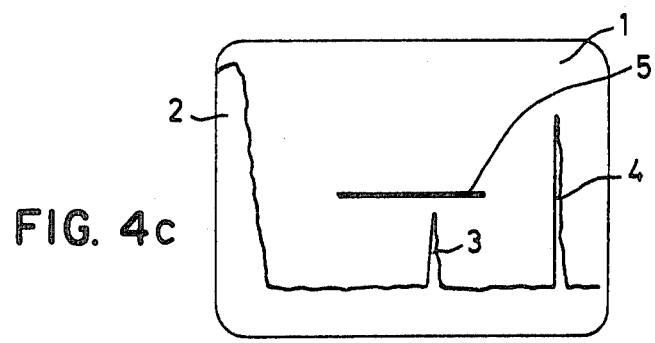
Figure 4D:
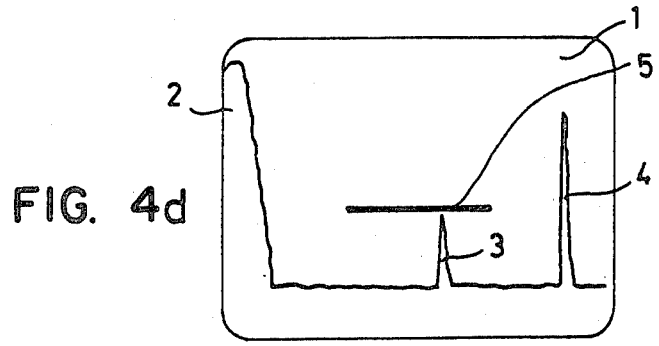

Next, as previously described, a comparison is made in comparator 17 and the reference voltage is either reduced by a quarter of the possible pulse height, FIG. 4b, if the comparator does not deliver any output signal within the time gate, or the reference voltage is increased by a quarter of the possible pulse height if the comparator delivers pulses to the flip-flop 232 during the time gate. During subsequent steps the reference voltage is increased or reduced by 1/8, 1/16, 1/32, 1/64 and 1/128 of the possible pulse height (FIGS. 4c–4d) until, after the seventh trigger pulse for example, the reference voltage has been brought sufficiently close to the peak pulse value to cause the reference voltage to be higher than the pulse peak value by the aforementioned one digital step within a few additional digital steps. Advantageously, this successive approximation is effected by microprocessor 233 (FIG. 3), in which case the connection 235 from the microprocessor to the D/A converter 231 must comprise a corresponding number of lines, e.g. eight conductors in the present case.

In another embodiment of the invention, for use more particularly in analog signal processing, a known peak detector is used. A peak detector of the aforementioned kind uses the charge of a capacitor and has been described e.g. by J. R. Naylor in Digital and Analog Signal Applications of Operational Amplifiers, IEEE Spectrum, June, 1971, pages 41/42. The aforestated peak detector, however, has a disadvantage in that the ultrasound pulse repeated in the time gate cannot be amplified and the measurements may be distorted by spurious pulses having a greater amplitude than the echo responsive signals to be measured.

Figure 5:
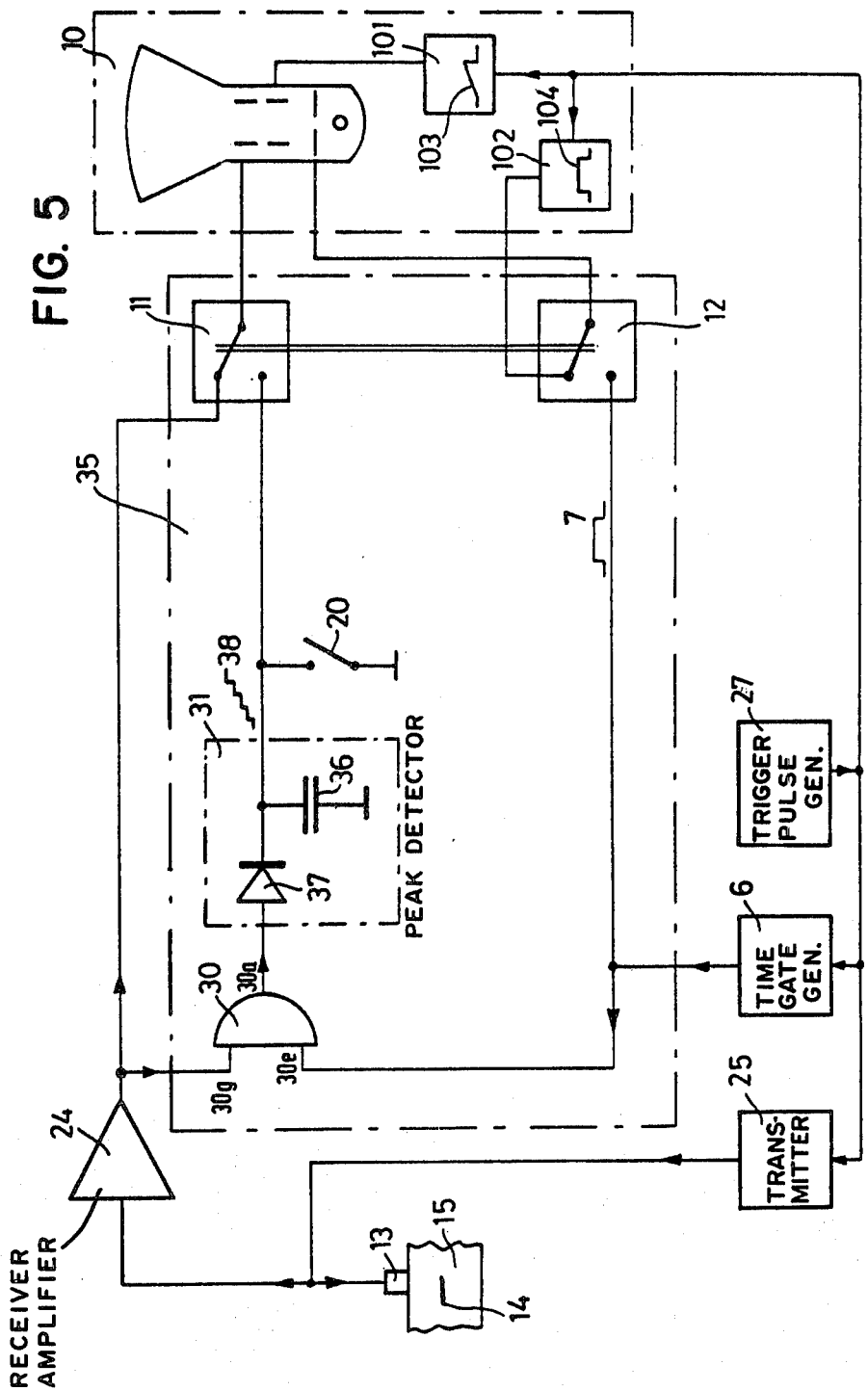
FIG. 5 shows an alternative embodiment of the invention.

FIG. 5 shows another embodiment of the invention. The drawing shows the following components of a conventional ultrasonic device; a trigger pulse generator 27, a pulse transmitter 25, a probe 13 coupled to a workpiece 15 having a reflector 14, a receiver amplifier 24, a time gate signal generator 6, a display stage 10 and sweep generator 101 for the display tube. In this embodiment of the circuit, the block marked 35 also comprises the following components: an AND gate 30, a peak detector 31 of a known kind and triggerable switches 11 and 12.

Figure 6:
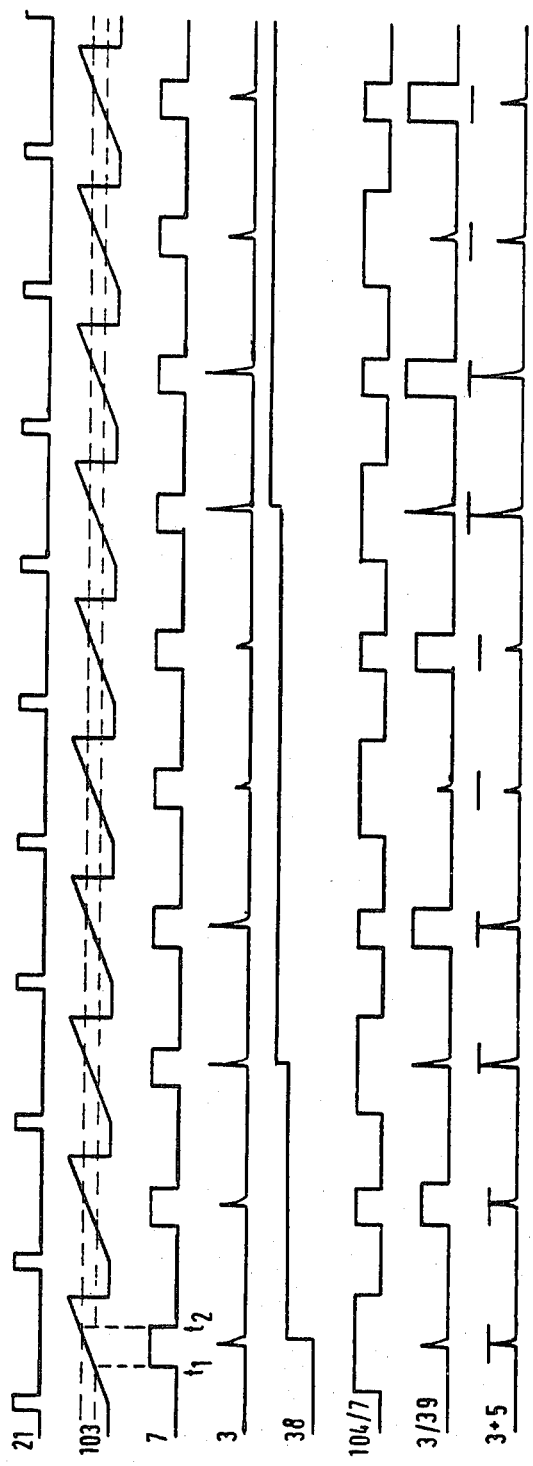
FIG. 6 is a pulse diagram pertaining to the embodiment per FIG. 5.

The construction and operation of this circuit are further illustrated by the pulse diagram in FIG. 6. In FIG. 6, the operation of gate 6 is represented by pulses 7. Trigger pulses 21 trigger repetitively the individual measuring processes. Ultrasonic pulses 3 are received during the time gate, i.e. the depth range under investigation. The line sweep for the tube 10 is represented by the sawtooth pulses 103. Voltage 38 is the corresponding voltage at the peak detector 31. At the output side of switch 11, the d.c. voltage at the display stage 10 is present only in pulse form, as shown by pulses 39. Line 3/39 represents the pulses imaged by the tube of stage 10 for each trigger process, and line 3+5 represents the pulse display perceived by the eye, the bar height 5 corresponding to the height of pulse 39. In FIGS. 5 and 6 and the description, reference is made only to the pulses 3 received within the time gate. Other pulses, such as the transmitted pulse, the echo pulse from the rear wall and other pulses outside the time gate, are of course present, but are not shown since they have no relevance to the present invention.

In the example per FIGS. 5 and 6, for displaying the peak pulse amplitude within a measuring period, the peak detector 31 is set to a low value by closing the switch 20. If switch 20 is opened and the receiver amplifier 24 delivers pulses, the pulses are applied to input 30g of AND gate 30. The time gate pulse 7 is applied to input 30e of the same AND gate, so that the received pulse, provided it occurs within the time gate range, can pass the AND gate 30 and is supplied to the peak detector 31.

Consequently, capacitor 36 is charged with the peak voltage of the pulse. Subsequent pulses having voltage peaks below the voltage charging the capacitor 36, have no influence on the charging voltage. Capacitor 36 therefore always remains charged to the highest peak voltage possessed by any pulse which has occured.

Each trigger pulse 21 actuates the sweep generator 101 for the display tube and triggers the time gate generator 6 for a workpiece depth range, so that gate generator 6 generates a pulse 7. The trigger pulse also changes switches 11 and 12, preferably in alternation. When the switches are in the top position, the normal ultrasonic pulse pattern is displayed on the screen, whereas when the switches are in the bottom position, the voltage 38 charging the peak detector 31 is displayed only during the time gate pulse 7; advantageously during this phase the display is not intensified by stage 102 but by the gate generator 6. Alternatively, transmitter 25 can easily be triggered in such a manner that it does not generate any ultrasonic pulses when the reference voltage 38 is displayed. The trigger pulse 21 is usually generated several hundred to several thousand times per second, so that as a result of the switching from displaying the echo to displaying the voltage 38, the eye cannot follow the change and the screen shows both the normal ultransonic pulse pattern and the voltage 38 at the peak detector. According to the invention, the voltage is shown as a horizontal bar 5 for the duration of the time gate, using the same screen height coordinates as the peak of the highest pulse amplitude which has occurred.

Figure 7:
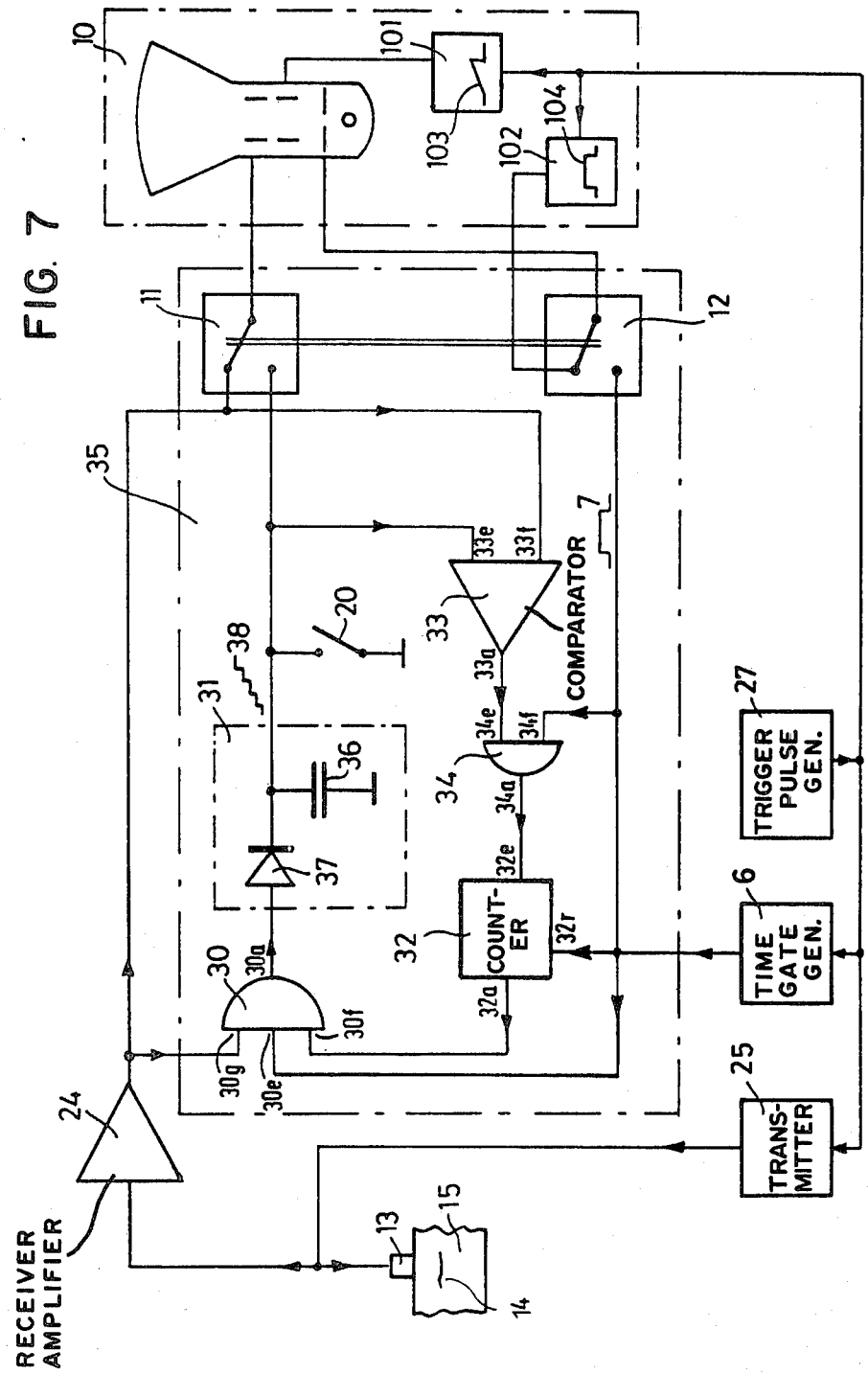
FIG. 7 is a block circuit diagram showing another embodiment of the invention requiring additional components.

In another embodiment of the invention, to prevent distortion of measurements by spurious pulses, the peak detector is supplied only with those pulses which occur N times in unbroken succession during the time gate of each triggering operation. The additional components required for this purpose, as shown in FIG. 7, are a pulse counter 32, an additional AND gate 34 and a comparator 33. The AND gate 30 has three inputs. In this modification, as before, switch 20 sets the peak detector 31 to a low value, the counter 32 being set at "zero" in accordance with its operation described hereinafter. When switch 20 is opened and the receiver amplifier 24 delivers pulses, they are also applied to input 33f of comparator 33. Comparator input 33e is supplied with a low voltage, since capacitor 36 has not yet been charged. The comparator thus transmits the pulses from the receiver and conveys them to input 34e of AND gate 34. Input 34f of the AND gate receives the time gate pulse 7, so that the received pulse, provided it comes within the gated range, can pass through the AND gate and is supplied to input 32e of counter 32. Counter 32 is designed so that it builds up a d.c. pulse at its output 32a if its input 32e is supplied with a pulse N times in succession, i.e. a pulse is supplied during successive gate signals 7 as sensed at input 32r. If at any time during a time gate pulse 7 the counter 32 does not receive a pulse at its input 32e, the counter switches back to its starting or "zero" position. The counter is thus designed so that its output 32a, and consequently the third input 30f of AND gate 30, receives an opening pulse provided a pulse 3 to be measured has been present during each time gate pulse, N times in succession. Input 30e of AND gate 30 is also supplied with gate pulse 7 and its input 30g is supplied with the pulses 3 delivered by receiver 24. Consequently, the gate output 30a delivers pulses from receiver 24 only if they occur within the time gate and are counted N times in succession by the counter 32. The peak detector 31 therefore is charged with the peak voltage of the pulse. Since the peak detector is also connected to comparator input 33e, advantageously only successive pulses exceeding the previously stored voltage level can reach counter 32 and will increase the charge on capacitor 36 only if the process has occurred N times in succession during N successive gated time intervals. Pulses having a voltage peak below the voltage stored on capacitor 36 cannot pass comparator 33. Hence, capacitor 36 always remains charged at the highest voltage heretofore possessed by a pulse which has repeated during each time gate, N times. If a spurious pulse having a higher peak voltage than the voltage on capacitor 36 occurs at any time during the time gate, it will be able to pass comparator 33 and AND gate 34 and be counted by counter 32. Since, however, it has been found by experience that a spurious pulse is not repeated in uninterrupted succession during each of N time gate intervals, a time gate will sooner or later be applied to counter 32 without a pulse occurring at input 32e, so that the counter is reset to "zero".

While there has been described and illustrated a preferred embodiment of the invention and additional modifications have been indicated and illustrated, it will be apparent to those skilled in the art that further changes and modifications can be made without deviating from the principle of the invention which shall be limited only by the scope of the appended claims.

What is claimed is:

1. An ultrasonic test instrument including pulse generator means for periodically applying electrical pulses to a test probe adapted to be coupled to a workpiece for causing ultrasonic search pulses to be transmitted into such workpiece; receiver means coupled to said probe for receiving echo pulses arising from the search pulses intercepting a defect in the workpiece; display means including a cathode ray tube for displaying on the screen of the tube said echo pulses; time gate means coupled to said pulse generating means and receiver means for causing repetitive gated time intervals for providing to the display means only such echo pulses which are received by said receiver means from a predetermined workpiece region; means coupled to said time gate means, said receiver means and said display means for causing said cathode ray tube screen to display a variable length horizontal gate bar the length of which is commensurate with the duration of said gated time interval, and the height of which above a zero line is commensurate with the value of a predetermined reference voltage provided by means for generating a reference voltage, the improvement comprising:

means coupled to said receiver means and said means for generating a reference voltage for causing repetitively received echo pulses within corresponding gated time intervals to be compared with an incrementally increasing reference voltage provided by said means for generating a reference voltage;

means coupled to said means for generating a reference voltage and said display means for causing said bar to be displayed on said screen at the height commensurate with the value of said reference voltage;

means for causing the height of said gate bar to be retained at a constant amplitude on said screen responsive to the amplitude of the echo pulse having the maximum amplitude relative to additional received echo pulses, and switch means coupled to said means for generating a reference voltage for resetting said reference voltage to said predetermined reference voltage.

2. An ultrasonic test instrument as set forth in claim 1, said means for generating a reference voltage comprising a threshold voltage generator the output voltage of which is applied via switching means to vertical deflection means of said cathode ray tube; an AND gate, and a comparator; said comparator receiving at one input echo pulses from said receiver means and receiving at the other input also said output voltage from said threshold generator; the output of said comparator being coupled to one input of said AND gate and the other input of said AND gate being coupled to said time gate means, and the output of said AND gate coupled to the input of said threshold generator for causing said threshold generator to increase its output voltage by a digital step when the AND gate provides an output signal.

3. An ultrasonic test instrument as set forth in claim 2, said threshold voltage generator comprising a microprocessor the output of which is coupled to a digital-to-analog converter.

4. An ultrasonic test instrument, as set forth in claim 1, the output of said time gate means being coupled to one input of and AND gate, the other input of said AND gate being coupled to said receiver means, the output of said AND gate being coupled to the input of a peak detector, and the output of said peak detector being coupled via switching means to vertical deflection means of said cathode ray tube.

5. An ultransonic test instrument as set forth in claim 4, said AND gate having three inputs, said third input being coupled via the series combination of a counter and comparator to the output of said peak detector, and the echo responsive pulse from said receiver means being coupled to one input of said comparator.

6. An ultrasonic test instrument as set forth in claims 4 or 5 and means causing the output of said peak detector and the echo pulses to be coupled to said vertical deflection means of said cathode ray tube in alternation or in synchronism with a line sweep voltage applied to said tube.

7. An ultrasonic test instrument as set forth in claim 3, and means causing the output of said threshold voltage generator and the echo pulses to be coupled to said cathode ray tube in alternation or in synchronism with a line sweep voltage applied to said tube.

8. An ultrasonic test instrument including pulse generator means for periodically applying electrical pulses to a test probe adapted to be coupled to a workpiece for causing ultrasonic search pulses to be transmitted into such workpiece; receiver means coupled to said probe for receiving echo pulses arising from the search pulses intercepting a defect in the workpiece; display means including a cathode ray tube for displaying on the screen of the tube said echo pulses; time gate means coupled to said pulse generating means and receiver means for causing repetitive gated time intervals for providing to the display means only such echo pulses which are received by said receiver means from a predetermined workpiece region; means coupled to said time gate means, said receiver means and said display means for causing said cathode ray tube screen to display a variable length horizontal gate bar the length of which is commensurate with the duration of said gated time interval, and the height of which above a zero line is commensurate with the value of a predetermined reference voltage provided by means for generating a reference voltage, the improvement comprising:

means coupled to said receiver means and said means for generating a reference voltage for causing repetitively received echo pulses within corresponding gated time intervals to be compared with an incrementally increasing reference voltage provided by said means for generating a reference voltage;

means coupled to said means for generating a reference voltage and said display means for causing said bar to be displayed on said screen at the height commensurate with the value of said reference voltage;

means for causing the height of said gate bar to be retained at a constant amplitude on said screen responsive to the amplitude of the echo pulse having the maximum amplitude relative to additional received echo pulses;

switch means coupled to said means for generating a reference voltage for resetting said reference voltage to said predetermined reference voltage;

a first AND gate having three inputs, the first input being coupled to the output of said time gate means, the second input being coupled to said receiver means, the third input being coupled via the series combination of a counter and comparator to the output of a peak detector, and the echo responsive pulse from said receiver means being coupled to one input of said comparator, the output of said first AND gate being coupled to the input of said peak detector, and the output of said peak detector being coupled via switching means to vertical deflection means of said cathode ray tube, and a further AND gate coupled serially between said comparator and said counter, said further AND gate having one input coupled to said gate means and another input coupled to the ouput of said comparator.

9. An ultrasonic test instrument including pulse generator means for periodically applying electrical pulses to a test probe adapted to be coupled to a workpiece for causing ultrasonic search pulses to be transmitted into such workpiece; receiver means coupled to said probe for receiving echo pulses arising from the search pulses intercepting a defect in the workpiece; display means including a cathode ray tube for displaying on the screen of the tube said echo pulses; time gate means coupled to said pulse generating means and receiver means for causing repetitive gate time intervals for providing to the display means only such echo pulses which are received by said receiver means from a predetermined workpiece region; means coupled to said time gate means, said receiver means and said display means for causing said cathode ray tube screen to display a variable length horizontal gate bar the length of which is commensurate with the duration of said gated time interval, and the height of which above a zero line is commensurate with the value of a predetermined reference voltage provided by means for generating a reference voltage, the improvement comprising:

means coupled to said receiver means and said means for generating a reference voltage for causing repetitively received echo pulses within corresponding gated time intervals to be compared with an incrementally increasing reference voltage provided by said means for generating a reference voltage;

means coupled to said means for generating a reference voltage and said display means for causing said bar to be displayed on said screen at the height commensurate with the value of said reference voltage;

means for causing the height of said gate bar to be retained at a constant amplitude on said screen responsive to the amplitude of the echo pulse having the maximum amplitude relative to additional received echo pulses;

switch means coupled to said means for generating a reference voltage for resetting said reference voltage to said predetermined reference voltage;

said means for generating a reference voltage comprising a threshold voltage generator the output of which is applied via switching means to vertical deflection means of said cathode ray tube;

and AND gate;

a comparator receiving at one input echo pulses from said receiver means and receiving at the other input said output voltage from said threshold voltage generator, the output of said comparator being coupled to one input of said AND gate and the other input of said AND gate being coupled to said time gate means, and the output of said AND gate being coupled to the input of said threshold voltage generator for causing said threshold voltage generator to increase its output voltage by a digital step when said AND gate provides an output signal;

said threshold voltage generator comprising a microprocessor the output of which is coupled to a digital-to-analog converter, and the coupling from said microprocessor to the digital-to-analog converter comprising a plurality of output lines by which the digital-to-analog converter first produces a reference voltage half as high as its possible final value, the voltage being compared with the amplitude of the echo pulse and then increased or decreased by half until the reference voltage is substantially equal to the amplitude of the echo pulse.

* * * * *